United States Patent
Lindh et al.

(10) Patent No.: US 8,768,443 B2
(45) Date of Patent: Jul. 1, 2014

(54) SYSTEM AND METHOD FOR DETERMINING ATRIAL ARRHYTHMIA BURDEN

(75) Inventors: Par Lindh, Maple Grove, MN (US); Donovan Benton Fellows, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1520 days.

(21) Appl. No.: 12/396,718

(22) Filed: Mar. 3, 2009

(65) Prior Publication Data
US 2009/0222056 A1    Sep. 3, 2009

Related U.S. Application Data

(60) Provisional application No. 61/033,301, filed on Mar. 3, 2008.

(51) Int. Cl.
    *A61B 5/04*    (2006.01)
(52) U.S. Cl.
    USPC .......................................................... 600/515
(58) Field of Classification Search
    USPC .................. 607/14, 15, 30; 600/515, 518
    See application file for complete search history.

(56) References Cited

U.S. PATENT DOCUMENTS

| | | | |
|---|---|---|---|
| 6,336,903 B1 | 1/2002 | Bardy | |
| 6,368,284 B1 | 4/2002 | Bardy | |
| 6,398,728 B1 | 6/2002 | Bardy | |
| 6,411,840 B1 | 6/2002 | Bardy | |
| 6,440,066 B1 | 8/2002 | Bardy | |
| 7,009,511 B2 | 3/2006 | Mazar et al. | |
| 7,265,676 B2 | 9/2007 | Gordon et al. | |
| 2003/0105491 A1 | 6/2003 | Gilkerson et al. | |
| 2006/0265016 A1* | 11/2006 | Kim et al. | 607/9 |

OTHER PUBLICATIONS

Euler, David E. et al., "Atrial Arrhythmia Burden as an Endpoint in Clinical Trials: Is it the Best Surrogate? Lessons from a Multicenter Defibrillator Trial", *Cardiac Electrophysiology Review* 2003 , 7: pp. 355-358.

* cited by examiner

*Primary Examiner* — Mark W Bockelman
(74) *Attorney, Agent, or Firm* — Pauly, DeVries Smith & Deffner, LLC

(57) ABSTRACT

A system and method for determining atrial arrhythmia burden is provided. Consecutive sets of parametric data regularly obtained from an implantable medical device through remote interrogation are centrally maintained. An atrial arrhythmia burden is determined. A cumulative atrial tachyarrhythmia (AT) duration is identified for each atrial arrhythmia episode recorded in the parametric data over a fixed look back period. One of an AT mode switch time and maximum atrial tachyarrhythmia AT duration are evaluated respectively subject to the duration between the consecutive sets being of sufficient length and a change having occurred to the maximum AT duration.

11 Claims, 11 Drawing Sheets

SYSTEM AND METHOD FOR DETERMINING ATRIAL ARRHYTHMIA BURDEN

This application claims the benefit of U.S. Provisional App. No. 61/033,301 filed Mar. 3, 2008, the content of which is herein incorporated by reference in its entirety.

FIELD

The invention relates in general to cardiac rhythm management and, specifically, to a system and method for determining atrial arrhythmia burden.

BACKGROUND

Implantable medical devices (IMDs) variously provide physiological data monitoring and therapy delivery, including cardiac defibrillation, pacing, and resynchronization therapy. Fully implanted IMDs function autonomously through preprogrammed control and often record patient physiometric information. The physiometry, as well as parametric data, can be respectively retrieved and downloaded by interfacing the IMD to programmers, repeaters, and similar external devices, which program, troubleshoot, and exchange the physiometry and parametric data through induction, radio frequency, or other wireless telemetry. Programmers are full-function interrogators designed for clinical use with a range of IMDs. In contrast, repeaters are limited-function interrogators, which are often matched to a specific IMD and are intended for remote at-home patient use.

Cardiac rhythm management (CRM) devices are a particular form of IMD, which provide therapeutic electrical stimuli to the heart in response to cardiac arrhythmias. Pacemakers, for instance, manage bradycardia, which is an abnormally slow or irregular heartbeat, by delivering pacing stimuli to restore normal sinus rhythm through electrodes provided on stimulation leads, such as endocardial or epicardial pacing leads. Implantable cardioverter defibrillators (ICDs) treat tachycardia, which are abnormally fast and life threatening heart rhythms, through high energy cardioversion, defibrillation shocks, or anti-tachycardia pacing. CRM devices also continually monitor and record patient physiometry and parametric data on therapy delivery, which are retrievable by caregivers through device interrogation.

Conventional arrhythmia management using CRM devices is episode-focused. Changes in heart rhythm are monitored by a CRM device as arrhythmic episodes potentially requiring therapy to convert, mitigate, or interrupt the change. When the magnitude or duration of an episode exceeds a fixed threshold, therapy may be delivered by the device. Arrhythmic episodes of duration shorter than the threshold are not considered actionable, even though of clinical importance to providing overall arrhythmia management.

The focus on episodes is dictated to some extent by device limitations. CRM devices are intended for long term implantation, yet have limited battery life and finite data storage capacity. Increasing discrimination over the selection of actionable episodes, such as through tiered therapy, preserves battery life and avoids patient discomfort from unnecessary treatments. Similarly, storing only those episodes that resulted in therapy delivery, plus a limited set of other non-actionable episodes, can conserve data storage. When no data storage remains, the oldest episodes are discarded to free storage space. As a result, the longer the time between CRM device interrogations, the more episodes may get discarded.

U.S. Pat. No. 7,265,676, issued Sep. 4, 2007 to Gordon et al., describes an alert system and method for an IMD, which detects the occurrence of an event for clinician attention. The IMD alerts on therapy delivery, arrhythmias, heart failure, system integrity, and cardiac ischemia events. The arrhythmic events include atrial and ventricular fibrillation, including non-sustained tachycardia. Cardiac signals are analyzed against an alert criterion before generating an alert from the IMD to patient or clinician. However, alert generation is limited to arrhythmic episodes identified in on-device data only.

Therefore, an approach is needed to provide identification of potentially arrhythmic conditions based on expanded device-originated physiometry and parametric data without excessive depletion of device resources.

SUMMARY

Embodiments herein include systems and methods of determining atrial arrhythmia burden based on data originating from episode duration and counter data. In an embodiment, a CRM device maintains a set of running tallies or counters of episode occurrences and durations. The durations of atrial tachyarrhythmia (AT) episodes and counters for total AT mode switch time, lifetime maximum AT duration, and reset maximum AT duration are then centrally tracked by periodically interrogating the CRM device through, for instance, a patient-operable at-home repeater. The data can be evaluated following each interrogation. The total duration of the AT episodes occurring in each period can be determined, provided the AT episode data is available and has not been lost, such as occurs when a CRM device discards least recent data to make storage space available for new data. Also, the total AT mode switch time, lifetime maximum AT duration, and reset maximum AT duration can be evaluated as they provide increasingly generalized, but useful, indications of AT duration relative to the next most recent interrogation.

One embodiment provides a system and method for determining atrial arrhythmia burden. Consecutive sets of parametric data regularly obtained from an implantable medical device through remote interrogation are centrally maintained. An atrial arrhythmia burden is determined. A cumulative atrial tachyarrhythmia (AT) duration is identified for each atrial arrhythmia episode recorded in the parametric data over a fixed look back period. At least one of an AT mode switch time and maximum AT duration are evaluated respectively subject to the duration between the consecutive sets being of sufficient length and a change having occurred to the maximum AT duration.

A further embodiment provides a system and method for identifying an atrial arrhythmia burden using a patient management system. A cardiac rhythm management (CRM) device implanted in a patient under remote patient management is periodically interrogated. A set of parametric data retrieved from each interrogation of the CRM device is stored into a centralized database. An atrial arrhythmia burden is determined. Parametric data sets are selected and include an earlier and a consecutive interrogation of the CRM device. Each atrial tachyarrhythmia (AT) duration recorded for atrial arrhythmia episodes in the parametric data sets is identified. A cumulative AT duration occurring within a fixed look back period of each AT episode is determined within the consecutive interrogations. AT mode switch times for each interrogation are compared. The AT mode switch times are averaged over the duration of the consecutive interrogations, subject to the duration being of sufficient length. Counters of at least one of lifetime maximum AT duration and reset maximum AT duration are compared. One of the lifetime maximum AT duration and reset maximum AT duration are selected upon identifying a change in each respective counter.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Clinical management of patients with atrial arrhythmia can be benefited by systems that assess atrial arrhythmia burden rather than simply reporting on discrete events. Atrial arrhythmia burden can be defined as the cumulative duration of all atrial arrhythmias occurring within a fixed time period divided by the total duration of the fixed time period. Frequently, the fixed time period is 24 hours, though many other fixed time periods may be used.

Embodiments herein can include systems and methods that can determine atrial arrhythmia burden by analyzing multiple data sources. The multiple data sources can include, but are not limited to, data regarding atrial tachyarrhythmia (AT) episodes (episodic data) as well as therapy counter data including total atrial tachyarrhythmia (AT) mode switch time, lifetime maximum AT duration, and/or reset maximum AT duration. Utilization of these various data sources can allow for robust identification of atrial arrhythmia burden. Atrial tachyarrhythmia (AT) episodes are recorded as beginning when the implanted device determines that an atrial tachyarrhythmia has begun and ending when the implanted device determines that the atrial tachyarrhythmia has ended. Criteria for the device to use when determining that an atrial tachyarrhythmia is present can be set by a system user, such as a physician. In some embodiments, the device can analyze electrical signals from cardiac tissue and be programmed with a nominal value of 170 beats per minute as the threshold value for declaring than an atrial tachyarrhythmia episode has begun. Various aspects of exemplary embodiments are described in greater detail below.

Environment

Figure 1:
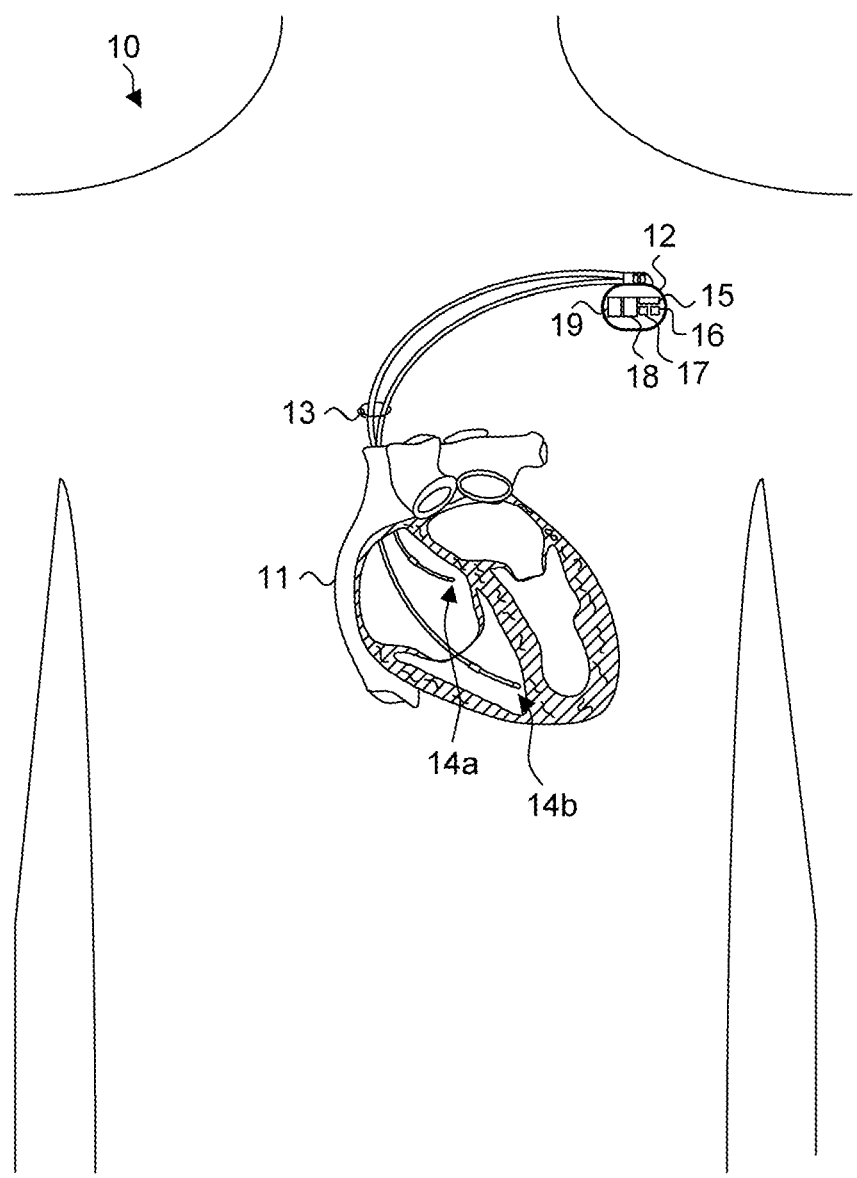
FIG. 1 is a block diagram showing, by way of example, an in situ CRM device with dual-chamber endocardial pacing leads.

Depending upon type, CRM devices generally provide therapeutic electrical stimuli into up to three chambers of the heart. Single-chamber CRM devices typically rely on one pacing lead attached to either the right atrium or right ventricle, while dual-chamber CRM devices utilize a pair of pacing leads attached to the right atrium and right ventricle. Triple-chamber CRM devices generally use pacing leads in the right atrium, right ventricle, and coronary venous system. FIG. 1 is a block diagram showing, by way of example, an in situ CRM device 12 with dual-chamber pacing leads 13. CRM devices can include pacemakers, implantable cardioverter-defibrillators, and cardiac resynchronization therapy (CRT) devices. Other CRM devices are possible.

The CRM device 12 is surgically implanted in the chest, abdomen, or other bodily location of a patient 10 and includes a pair of pacing leads 13 for providing monitoring within and for delivering therapy to the patient's heart 11. Electrical stimuli are delivered through electrodes 14a, 14b on the distal end of each pacing lead 13. The CRM device 12 also encloses operational circuitry within a hermetically-sealed housing, which generally includes a transducer 15; oscillator 16; control circuitry 17; memory 18; and power source 19, which provides a finite power supply for the operational circuitry. The transducer 15 provides signal conversion. The oscillator 16 regulates internal device operation by controlling the timing of IMD operations. The control circuitry 17 implements the device's functionality, such as therapy delivery or physiometric monitoring. The CRM device 12 can identify arrhythmia within the patient it is implanted in. As just one example, the CRM device 12 can identify episodes of atrial tachyarrhythmia by monitoring P to P intervals electrocardiogram data as sensed through electrodes, such as electrodes on the pacing leads 13. Many other techniques of sensing tachyarrhythmia episodes can also be used by the device. Finally, the memory 18 stores recorded data, such as the patient's monitored physiometry; environmental data, for instance, ambient temperature or time of day; and parametric information, including programming, status, and device operational characteristics. The parametric information also includes arrhythmic episode duration and counter data from which atrial arrhythmia burden can be determined, as further described below beginning with reference to FIG. 3.

Figure 2:
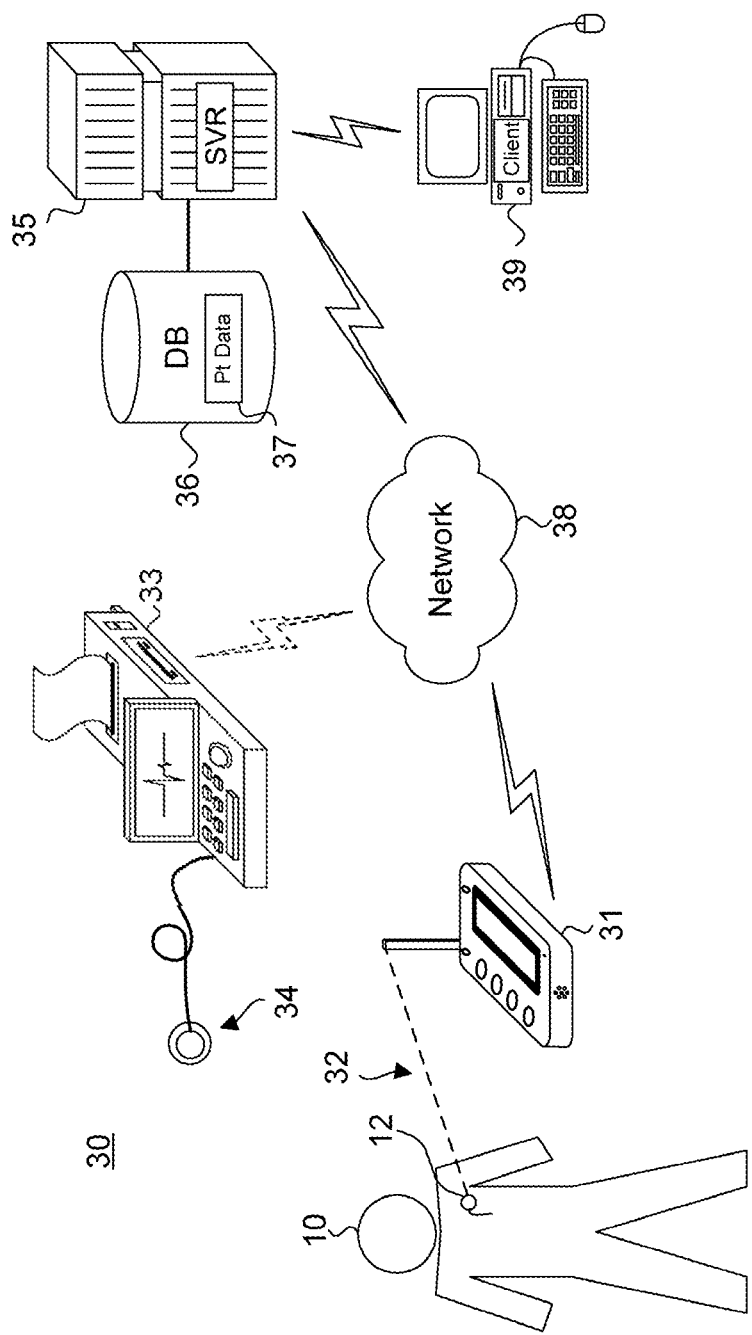
FIG. 2 is a block diagram showing, by way of example, an environment for remote wireless interrogation of a CRM device.

Periodically, the CRM device 12 is interrogated by an external device to retrieve recorded data and download programming. FIG. 2 is a block diagram showing, by way of example, an environment 30 for remote wireless interrogation of a CRM device 12. In addition to the CRM device 12, the environment 30 can include a repeater 31 or other patient-operable IMD interrogation device. The repeater 31 regularly interrogates the CRM device 12 through wireless or inductive telemetry 32 or other interfacing, either automatically, per a schedule, or on demand under patient or attendant control. Interrogations can be performed on a monthly, weekly, or daily basis, or as frequently as appropriate or practical. The repeater 31 can either store downloaded data locally, or can connect to the network 38 to store the downloaded data in the database 36. Periodic interrogation using a repeater 31 permits device-originated physiometry and parametric data to be stored off-device more frequently than otherwise permitted through use of a programmer 33 alone. Data loss due to lack of available on-device data storage is also minimized.

Additionally, the environment 30 generally includes a centralized server 35 coupled to a database 36 within which patient data 37 is stored. The server 35 can include a processor, amongst other components. The repeater 31 remotely interfaces with the server 35 to exchange the recorded data and programming through a network 38, such as a publicly available wide area network, including the Internet. Other forms of remote server interfacing are possible, such as described in related commonly-owned U.S. Pat. No. 7,009,511, to Mazar, issued Mar. 7, 2006, the disclosure of which is incorporated by reference.

In addition, caregivers, particularly cardiologists and electrophysiologists, are able to access the patient data 37 through a client 39 or other system interfaced to the server 35. The caregivers can also separately interrogate the CRM device 12 directly using a conventional programmer 33 that utilizes inductive or wireless telemetry 34 or other interfacing. The programmer 33 can either store downloaded data locally, or can connect to the network 38 to store the downloaded data in the database 36. Programmer interrogations generally occur at the initiative of a caregiver and outside the direction of the server 35. As a result, the server 35 may not be aware that a programmer-initiated interrogation occurred. Other caregiver devices and functions are possible.

In a further embodiment, the patient data 37 can be evaluated by the CRM device 12, repeater 31, programmer 33, server 35, or other external device for the occurrence of one or more chronic or acute health conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 4, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference. It will be appreciated that external patient management systems of embodiments herein can include one or more of repeater 31, programmer 33, server 35, and database 36.

In a still further embodiment, the patient data 37 is extracorporeally safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Exemplary Parametric Data

Figure 3:
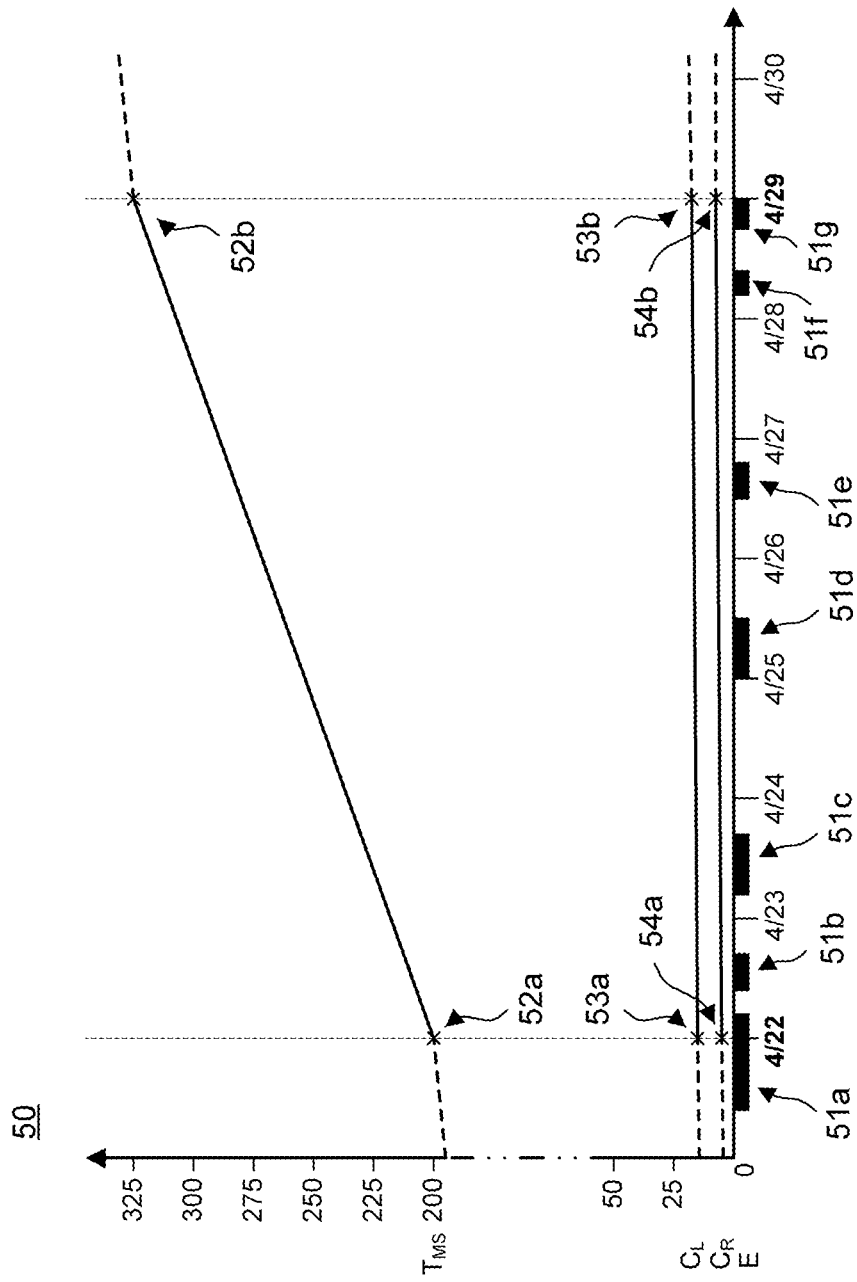
FIG. 3 is a graph showing, by way of example, arrhythmic episode duration and counter data from consecutive parametric data sets.

The parametric data maintained by a CRM device can include timers and counters for respectively tracking arrhythmic episode and therapy duration values, which are retrieved as a set of data during each interrogation of the CRM device. FIG. 3 is a graph 50 showing, by way of example, hypothetical arrhythmic episode duration and counter data from consecutive parametric data sets. The x-axis represents time in days and the y-axis represents counter values. Other data representations are possible.

The data sets are identified by date of retrieval, although other manners of data set identification are possible. Depending upon their type, parametric data can be recorded by duration, which can include a starting and ending time, or as an on-going tally. Other forms of parametric data recordation are possible.

In the example of FIG. 3, the CRM device was interrogated on April 22 ("4/22") and again on April 29 ("4/29"). The durations of all AT episodes 51a-51g that have occurred since the last interrogation were recorded by starting and ending times. The values for the therapy duration counters including total AT mode switch time 52a, 52b; lifetime maximum AT duration 53a, 53b; and reset maximum AT duration 54a, 54b were recorded as counter values.

In the example of FIG. 3, the seven AT episodes occurred between April 22 and April 29, with the first episode being in-progress from the previous day (e.g. April 21). The total AT mode switch time increased from 200 hours to 326 hours. The lifetime maximum AT duration increased from 16 hours to 18 hours. Finally, the reset maximum AT duration increased from 3 hours to 6 hours. Other types and values of parametric data are possible.

AT episode durations 51a-51g can be continually tracked during CRM device operation. In some embodiments, the therapy duration counters 52a-52b, 53a-53b, 54a-54b are only changed or incremented as necessary. As a result, the values of the therapy duration counters may vary between interrogations, although the date and time at which a particular counter changed may or may not be recorded by the implanted device. However, the values for the therapy duration counters at the time of device interrogation can be stored externally along with the date and/or time of the interrogation allowing changes in such values over time to be assessed. Thus, periodically retrieving the therapy duration counters though the use of a repeater 31 enables a date and time to be associated with each therapy duration counter, which might otherwise be unknown were use of the therapy duration counters be made by the CRM device alone. Moreover, periodic retrieval of data from the CRM device lessens or eliminates the loss of AT episode data.

Method for Atrial Arrhythmia Burden Detection

Figure 4:
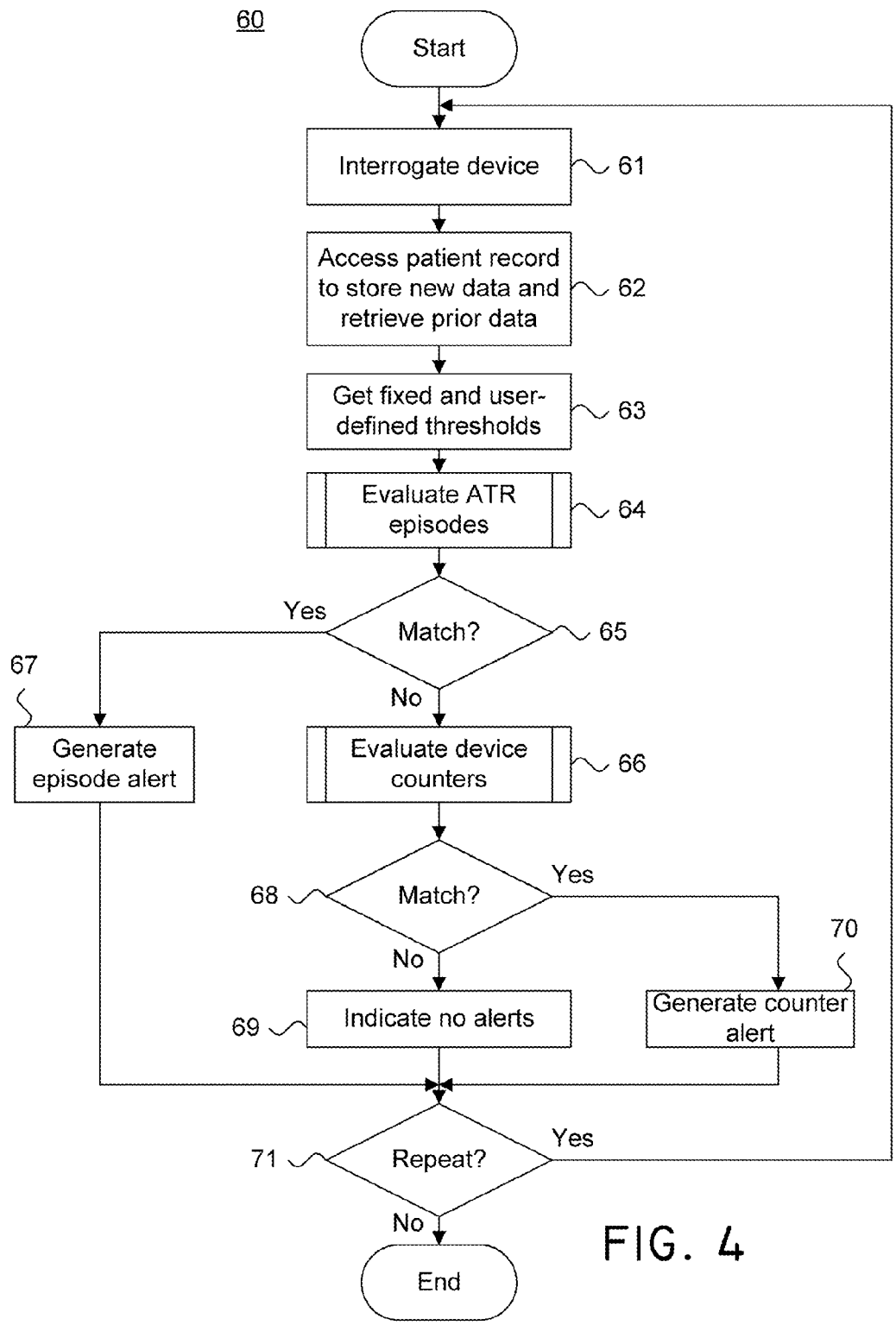
FIG. 4 is a flow diagram showing a method for determining atrial arrhythmia burden, in accordance with one embodiment.

Both the arrhythmic episode and the therapy duration counter data can facilitate atrial arrhythmia burden identification. The patient data 37 maintained in the database 36 (shown in FIG. 2) effectively expands the scope of data to be analyzed for atrial arrhythmia burden evaluation to include information beyond the limited data available to a CRM device. FIG. 4 is a flow diagram showing a method 60 for determining atrial arrhythmia burden, in accordance with one embodiment. The method 60 is performed as a series of process steps or operations by the server 35, or other general purpose programmable computing device having access to the database 36.

Atrial arrhythmia burden identification evaluation can be performed as a continuous cycle (steps 61-71). During each iteration, a patient's CRM device is interrogated by a repeater 31 (step 61) or other suitable device, generally per a schedule, or as requested or required. Upon upload of the arrhythmic episode data and the therapy duration counter data from the CRM device, the patient record is accessed in the database 36 to store the newly retrieved data and to retrieve previously-stored data (step 62). Additionally, both fixed and/or user-defined thresholds are obtained (step 63). For example, a standard 24-hour alert threshold may be applied when identifying episodes of atrial arrhythmia, while a user-specified alert threshold may be used to determine actual burden.

The arrhythmic episode and the therapy duration counter data from the interrogation and, if needed, the database 36 are then evaluated (steps 64-66). The AT episodes 51a-51g can be evaluated first (step 64), as further described below with reference to FIG. 5. If one or more AT episodes 51a-51g provide a match indicating that a threshold of atrial arrhythmia burden has been met (step 65), an alert can generated (step 67). For example, if analysis of the AT episodic data reveals that atrial arrhythmia has occurred for at least a threshold amount of time within a fixed time window, an atrial arrhythmia burden alert can be generated. An alert is an indication that a condition has been satisfied or a threshold exceeded, and is used by the server 35, or other device having access to the database 36, for triggering an action or interrupting a process. Other types of alerts and responses to alerts are possible. By way of example, audible alarms, phone calls, e-mail messages, fax messages, or the like can be initiated as part of an alert or a response to an alert.

A risk of data loss may occur if the storage space within the CRM device is full of AT episodes with no further storage space to store new AT episodes. Generally, if no data storage remains within the CRM device, the oldest AT episodes are discarded to free storage space. However, a complete lack of AT episodes 51a-51g generally means that no arrhythmic episodes occurred since the last interrogation.

In the absence of finding a match based on evaluation of AT episodes (step 65), therapy duration counter data can be analyzed in order to assess whether or not a threshold of atrial arrhythmia burden has been met. For example, the total AT mode switch time 52a, 52b, lifetime maximum AT duration counter 53a, 53b, and reset maximum AT duration counter 54a, 54b can be evaluated as further inquiries to determine atrial arrhythmia burden (step 66), as further described below beginning with reference to FIG. 6.

If one or more of the device counters provide a match indicating that an atrial arrhythmia burden threshold has been met (step 68), an alert is generated (step 70). Otherwise, an indication that no alerts were generated can be provided (step 69). The cycle can be again repeated (step 71) until terminated by user instruction or other condition. Other operations are possible.

It will be appreciated that the threshold amount of atrial arrhythmia burden that must be met before an alert is issued can be preconfigured or can be selected by a system user. For example in some embodiments, the atrial arrhythmia burden threshold can be preconfigured as greater than or equal to 6 hours of atrial arrhythmia in a 24 hour period (equal to an atrial arrhythmia burden of 25%). In some embodiments, the atrial arrhythmia burden threshold can be preconfigured as greater than or equal to 8 hours of atrial arrhythmia in a 24 hour period (equal to an atrial arrhythmia burden of 33%). Any desired level of atrial arrhythmia burden can be set as the threshold. In various embodiments, the denominator for calculation of arrhythmia burden is greater than or less than 24 hours.

Atrial Tachyarrhythmia (AT) Episode Evaluation

Figure 5:
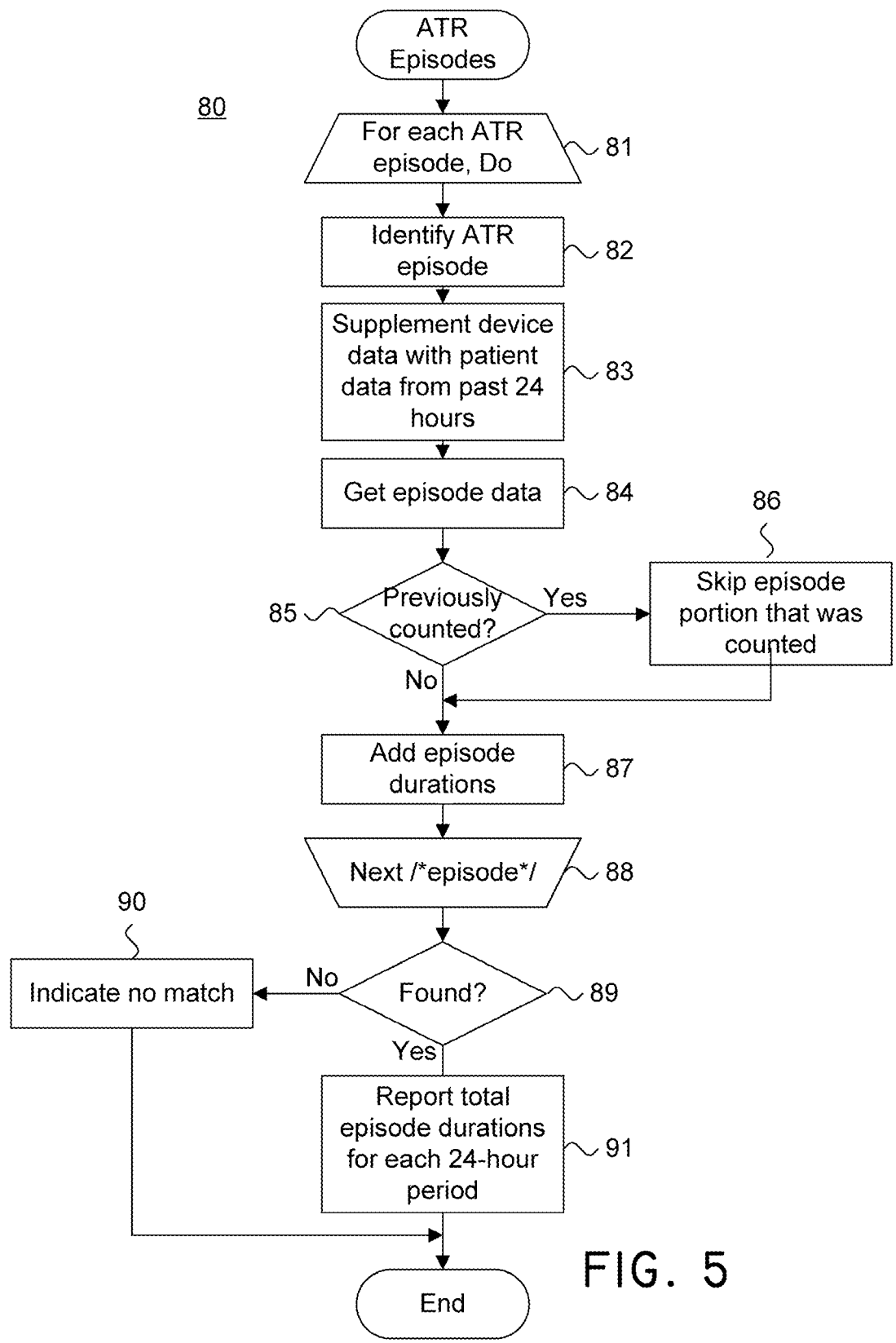
FIG. 5 is a flow diagram showing a routine for evaluating AT episodes for use with the method of FIG. 4.

The AT episode data includes the starting and ending times of each atrial arrhythmia episode. The AT episode is recorded, whether resulting in therapy delivery or not. FIG. 5 is a flow diagram showing a routine 80 for evaluating AT episodes for use with the method 60 of FIG. 4. AT episodes 51a-51g, whether exceeding or below a predetermined therapy threshold, can collectively contribute to overall atrial arrhythmia burden determination.

Each AT episode 51a-51g is evaluated (steps 81-88). The process begins with identification and evaluation of the most recent AT episode that occurred since the last interrogation (step 81). In subsequent evaluation cycles, the next most recent AT episode is identified and evaluated (step 81) until all AT episodes have been processed.

Each individual AT episode is evaluated in the context of a standard look back window. In some embodiments, the look back window is 24 hours, although other sizes of look back window are possible. For example, if the atrial arrhythmia burden threshold is set to be analyzed based on a 36 hour period, then the look back window can be 36 hours. The device data from the CRM device interrogation can be supplemented with patient data 37 retrieved from the database 36 (shown in FIG. 2) if necessary in order to provide sufficient data for the look back window (step 83) for each AT episode.

By way of example, referring back to FIG. 3, in response to the interrogation of April 29, the first evaluation cycle can look backward in time based on the AT episode 51g. The look back window can be measured from the end of the most recent episode (e.g. 51g) or the time of interrogation if the most recent episode is ongoing. Assuming the look back window is 24 hours, the look back window would sweep in both AT episodes 51f and 51g. However, in the next evaluation cycle when the end of episode 51f serves as the leading edge of the look back window, then only AT episode 51f is included if the look back window is 24 hours.

Next, data for all AT episodes within each look back window, including duration for each AT episode, are obtained (step 84). To avoid double-counting and redundant alert generation, those portions of an AT episode that were previously counted (step 85) during a prior interrogation can skipped (step 86) in some embodiments. For instance, an AT episode that was in-progress at the time of an interrogation would have an overall duration that included a portion of the episode that occurred prior to and a portion of the episode that occurred after the interrogation. Each portion can be counted as separate data separated by the interrogation.

The adjusted durations of the AT episodes occurring within the 24-hour look back window for each AT episode are added (step 87). In this manner the total amount of time taken up by AT episodes within the look back window can be assessed.

The evaluation cycle is repeated for each of the AT episodes that were recorded since the last interrogation (step 88). The system can evaluate if any AT episodes were found (step 89). If no AT episodes were found, an indication that no match was determined is generated (step 90). Otherwise, the total duration of the AT episodes occurring in each 24-hour period are reported (step 91). Thereafter, the system can assess whether or not the atrial arrhythmia burden threshold has been met during any 24-hour period. The subroutine can thereafter terminate.

In some embodiments, if an AT episode is in progress at the time of device interrogation, then the device interrogation time can be taken as the end of the AT episode for purposes of analyzing the duration of the AT episode.

Therapy Duration Counter Data Evaluation

Figure 6:
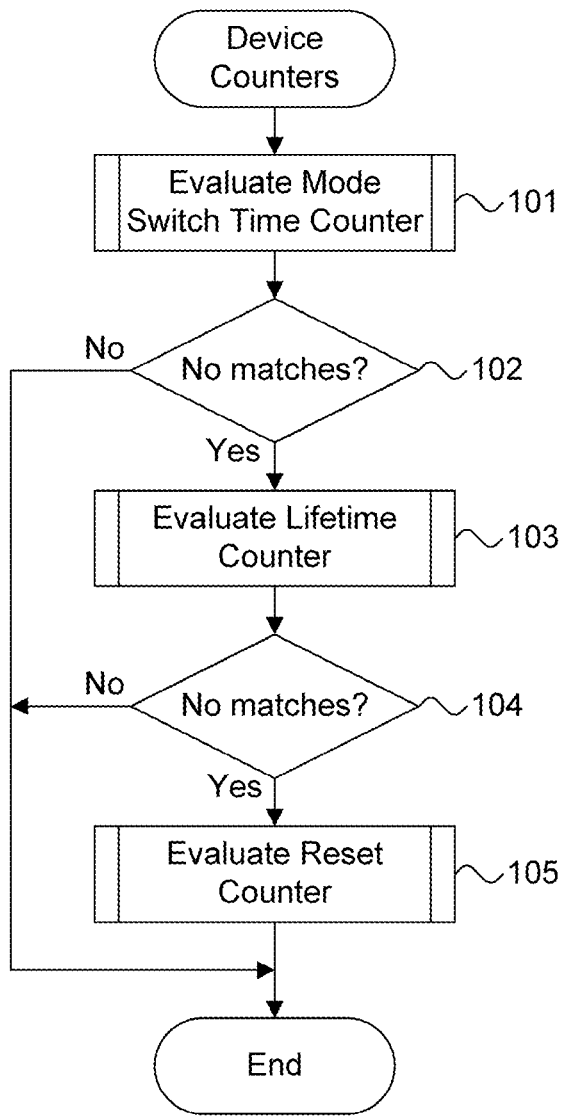
FIG. 6 is a flow diagram showing a routine for evaluating device counters for use with the method of FIG. 4.

As described above, therapy duration counter data can include the total AT mode switch time 52a, 52b; lifetime maximum AT duration 53a, 53b; and reset maximum AT duration 54a, 54b. Analysis of these therapy counter data can provide approximations of atrial arrhythmia burden with varying degrees of precision and can thus supplement analysis of AT episodic data. FIG. 6 is a flow diagram showing a routine 100 for evaluating therapy counter data for use with the method 60 of FIG. 4. In an embodiment, the device counters can be evaluated in order of total AT mode switch time, lifetime maximum AT duration counter, and reset maximum AT duration counter, which reflects decreasing certainty in the atrial arrhythmia burden determination. However, the evaluations could be performed in a different order, or as a subset of only one or two evaluations.

Figure 7:
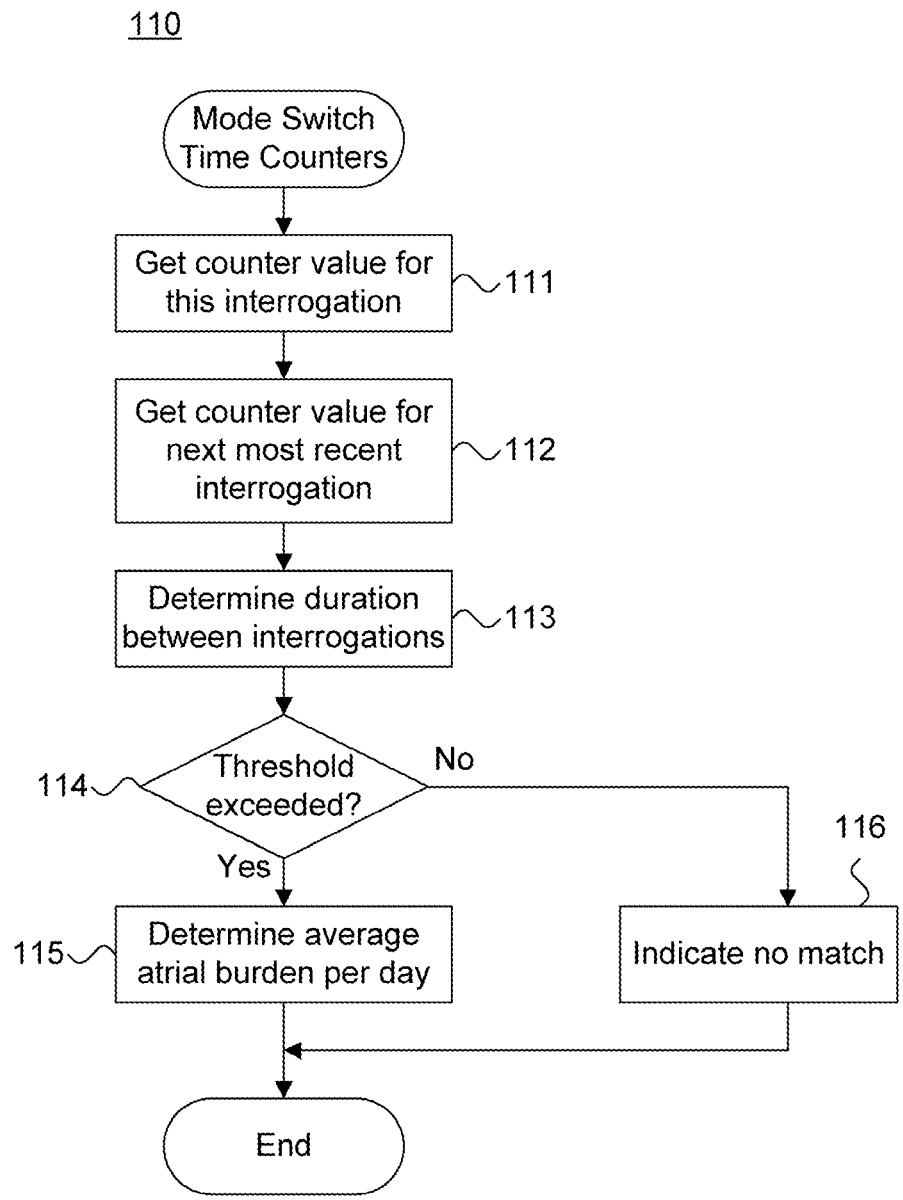
FIG. 7 is a flow diagram showing a routine for evaluating total AT mode switch time counters for use with the routine of FIG. 6.

In a particular embodiment, the total AT mode switch time 51a, 51b is evaluated first (step 101), as further described below with reference to FIG. 7. If evaluation of the total AT mode switch time cannot provide a match indicating that an atrial tachyarrhythmia burden threshold was not exceeded (step 102), then the lifetime maximum AT duration counter 53a, 53b can be evaluated (step 103), as further described below with reference to FIG. 8. If evaluation of the lifetime maximum AT duration cannot provide a match indicating that an atrial tachyarrhythmia burden threshold was not exceeded (step 104), then the reset maximum AT duration counter 54a, 54b can be evaluated (step 105), as further described below with reference to FIG. 9. The subroutine can thereafter terminate.

Total AT Mode Switch Time

The total AT mode switch time counter tracks a cumulative tally of the number of hours during which the CRM device deemed that atrial tachyarrhythmia was taking place. FIG. 7 is a flow diagram showing a routine 110 for evaluating total AT mode switch time counters for use with the routine 80 of FIG. 6. In some embodiments, the total AT mode switch time 51a, 51b does not reflect when each AT episode occurred, nor individual duration. However, the total AT mode switch time 51a, 51b will enable determination of the average number of seconds, minutes, hours, or other time metric per day spent in AT mode.

The total AT mode switch time 51a, 51b for the current and next most recent interrogations are obtained (steps 111, 112, respectively). The total time elapsed between the interrogations is determined (step 113). In some embodiments, a minimum length of time between the interrogations for total AT mode switch time can be specified as an interrogation time threshold. This can be useful to guard against spurious results from, for instance, rounding errors and edge cases. For example, in some embodiments an interrogation time threshold of at least 24 hours can be used, although other values are possible. That is, if the time between the current interrogation and the next most recent interrogation is less than 24 hours, analysis of total AT mode switch time may not result in an atrial tachyarrhythmia alert being generated, despite the calculated atrial tachyarrhythmia burden. However, if the interrogation time threshold is exceeded, that is, the duration between interrogations was sufficiently long (step 114), the average atrial arrhythmia burden can be determined (step 115) by dividing the difference of the total AT mode switch time counters by the total number of hours in the duration. If the threshold was not exceeded (step 114), an indication that no match was determined can be generated (step 116). The subroutine can thereafter terminate.

Lifetime Maximum AT Duration

Figure 8:
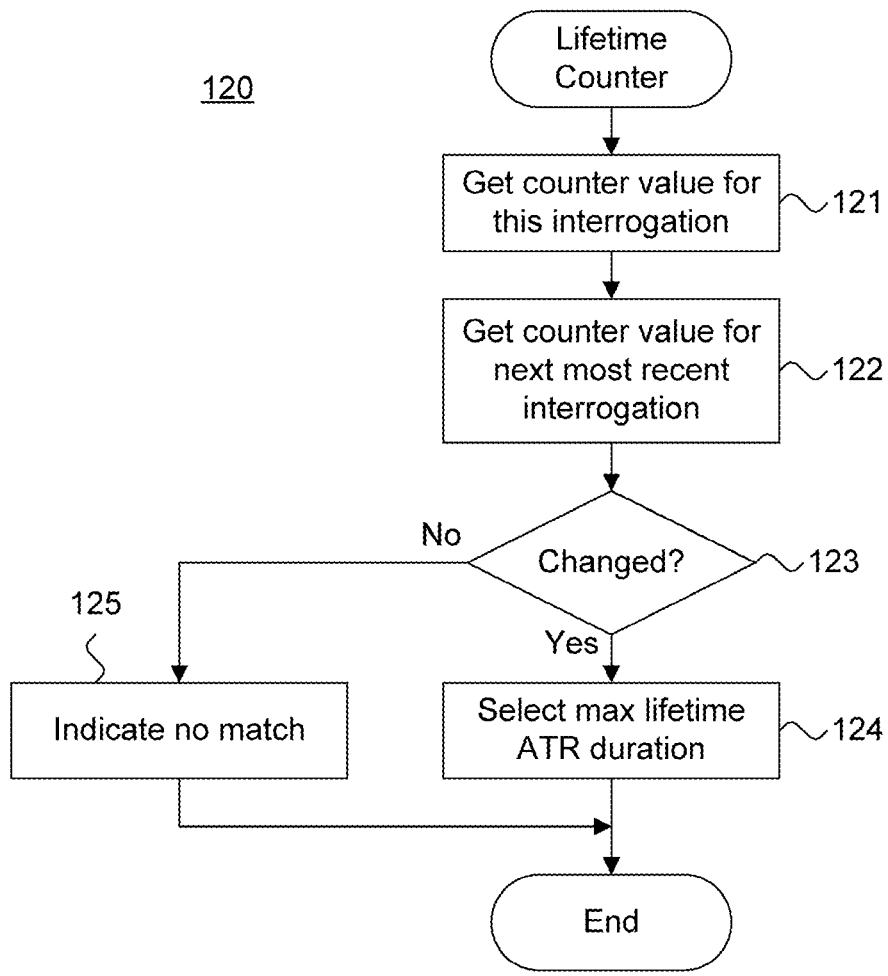
FIG. 8 is a flow diagram showing a routine for evaluating lifetime maximum AT duration counters for use with the routine of FIG. 6.

The lifetime maximum AT duration counter tracks the longest duration of an AT episode that the CRM device has observed since being implanted. FIG. 8 is a flow diagram showing a routine 120 for evaluating lifetime maximum AT duration counters for use with the routine 100 of FIG. 6. If the lifetime maximum AT duration counter has changed since the last interrogation, this indicates that the longest recorded AT episode yet observed occurred sometime since the last interrogation.

The lifetime maximum AT duration 52a, 52b for the current and next most recent interrogations are obtained (steps 121, 122, respectively). A determination can only be made if the lifetime maximum AT duration has actually changed (step 123), after which the value of the counter from the current interrogation is selected as the maximum AT duration (step 124). If the value has changed, then atrial arrhythmia burden can be determined based on the value for lifetime maximum AT duration. For example, referring back to the data of FIG. 3, the lifetime maximum AT duration increased from 16 to 18 hours. As such, it can be logically determined that an AT duration of 18 hours occurred at some point since the last interrogation. If 18 hours of atrial arrhythmia exceeds the atrial arrhythmia burden threshold, then a match is determined and an alert can be generated. Otherwise, an indication that no match was determined is generated (step 125). The subroutine can thereafter terminate.

Reset Maximum AT Duration

Figure 9:
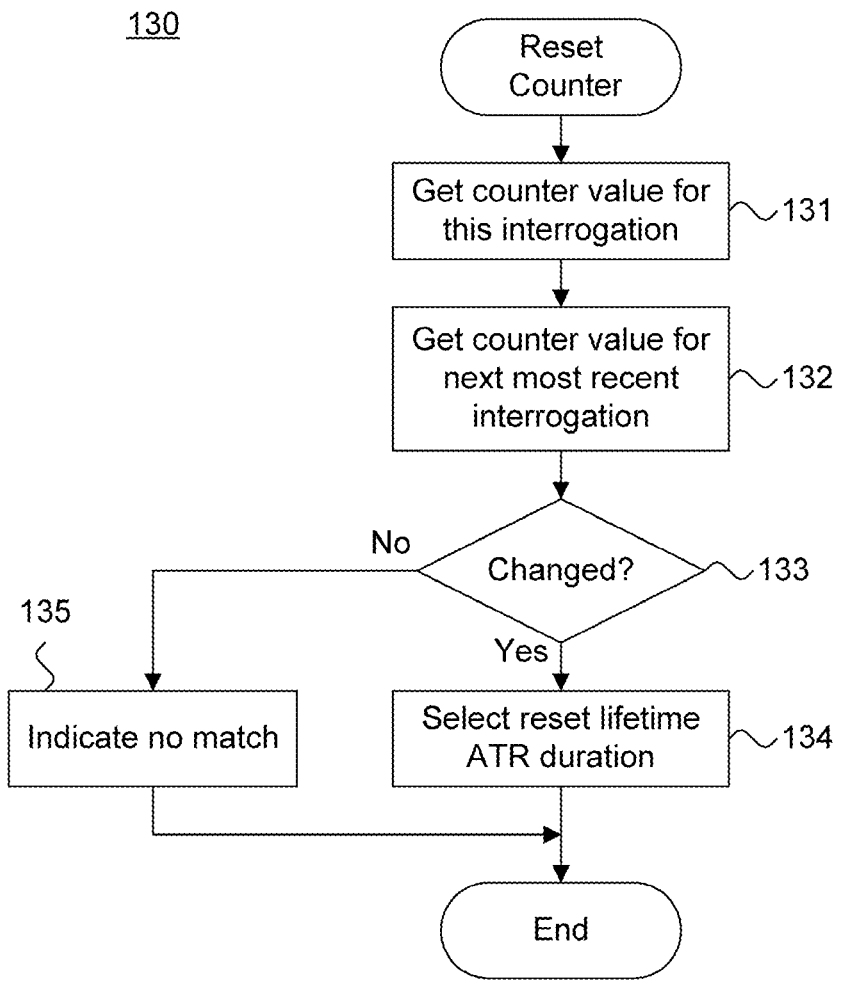
FIG. 9 is a flow diagram showing a routine for evaluating reset maximum AT duration counters for use with the routine of FIG. 6.

Some counters maintained by the implantable device can be reset during clinical visits. One example of a counter that can be reset is the reset maximum AT duration counter. The reset maximum AT duration counter tracks the longest duration of an AT episode which the CRM device has observed since last being reset. FIG. 9 is a flow diagram showing a routine 130 for evaluating reset maximum AT duration counters for use with the routine of 100 FIG. 6. Programmer-initiated interrogations that occur at any time between periodic interrogations, which can cause changes to the CRM device that were not reported to the server 35. For instance, the reset maximum AT duration counter could be reset by a programmer 33. If the counter has changed at the next regular interrogation, a reset of the counter can be inferred and the new counter value could be used as a maximum AT duration.

The reset maximum AT duration 53a, 53b for the current and next most recent interrogations are obtained (steps 131, 132, respectively). A determination can only be made if the reset maximum AT duration has actually changed (step 133), after which the value of the counter from the current interrogation is selected as the maximum AT duration occurring since reset (step 134). For example, referring back to the data of FIG. 3, the reset maximum AT duration increased from 3 hours to 6 hours. As such, it can be logically determined that an AT duration of 6 hours occurred at some point since the last interrogation. If 6 hours of atrial arrhythmia exceeds the atrial arrhythmia burden threshold, then a match is determined and an alert can be generated. Otherwise, an indication that no match was determined is generated (step 135). The subroutine can thereafter terminate.

In some implementations, therapy duration counters, such as lifetime maximum AT duration and reset maximum AT duration, are not updated until after an atrial tachyarrhythmia episode ends. As such, circumstances may arise wherein analysis of episodic data leads to an atrial tachyarrhythmia burden alert being issued and subsequent analysis of therapy duration counter data leads to a second atrial tachyarrhythmia alert being issued as a false positive based on overlapping information. For example in a scenario where the threshold for an atrial tachyarrhythmia burden is 6 hours in a 24 hour period, and where an atrial tachyarrhythmia episode has been in progress for 7 hours at the time of an interrogation and continues thereafter for 2 more hours, a first atrial tachyarrhythmia burden alert will be issued based on analysis of the episodic data at the time of the first interrogation because of the first 7 hours of the episode. After the episode ends, then the therapy duration counters are updated. Then, during the next evaluation cycle a second atrial tachyarrhythmia alert (false positive) may be issued on the basis of either lifetime maximum AT duration or reset maximum AT duration. In effect, then, two alerts may be generated based on a single long episode.

In some embodiments, subroutines can be included to prevent issuance of false positive alerts. In an embodiment, after finding that a atrial tachyarrhythmia burden threshold has been met based on analysis of lifetime maximum AT duration or reset maximum AT duration, the system can check to see if an alert was issued in the previous evaluation cycle, and if it was, then the subroutine can prevent an alert from issuing in the current evaluation cycle based on analysis of therapy counter data such as lifetime maximum AT duration and reset maximum AT duration.

System

Figure 10:
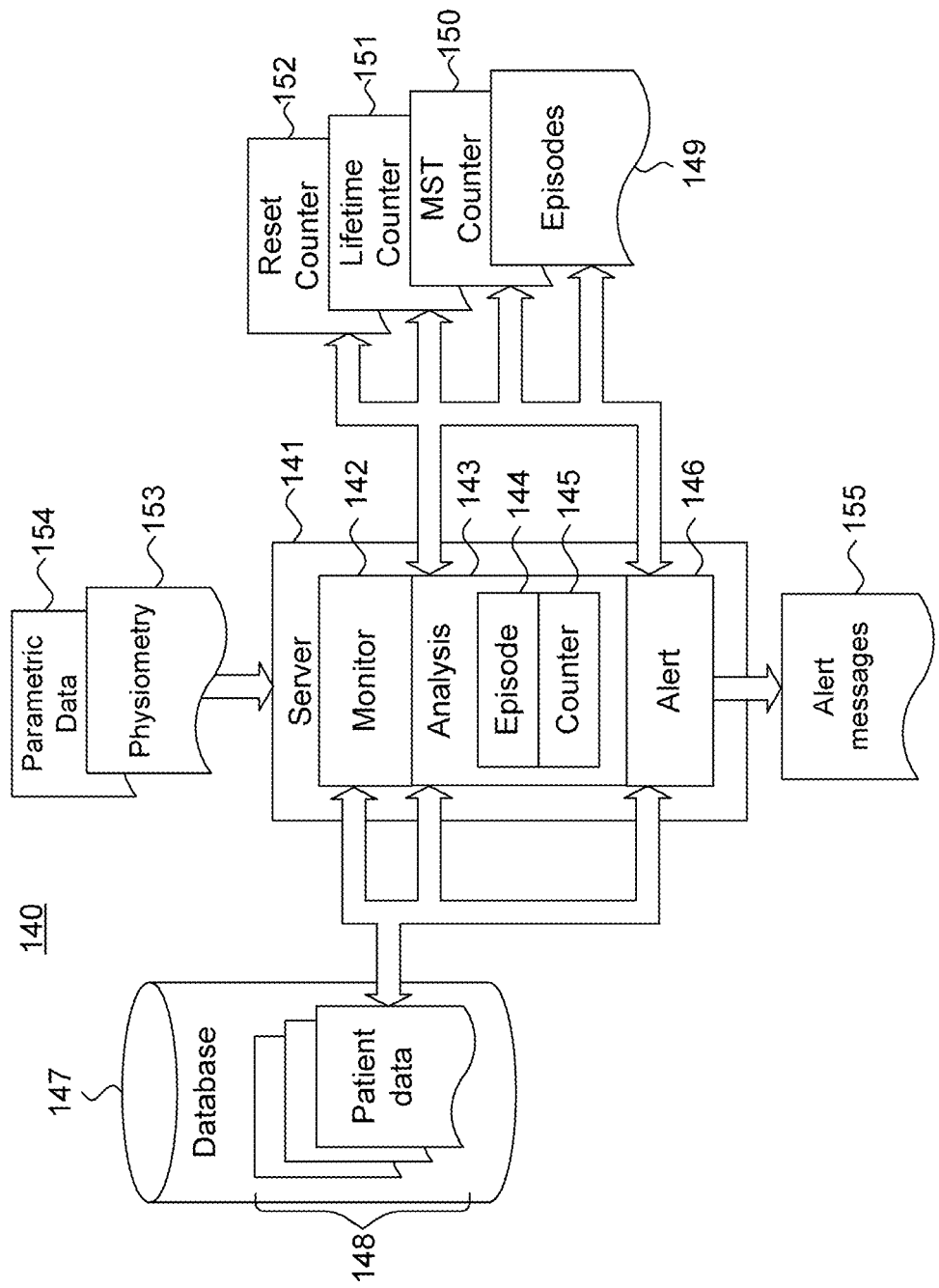
FIG. 10 is a functional block diagram showing a system for determining atrial arrhythmia burden, in accordance with one embodiment.

Atrial arrhythmia burden can be evaluated by a system having access to a database of regularly uploaded patient data. FIG. 10 is a functional block diagram showing a system 140 for determining atrial arrhythmia burden, in accordance with one embodiment. The system 140 can be a remote patient evaluation system. In some embodiments, the system includes a centralized server 141 that can perform the evaluation as described herein, but other systems or processing platforms are possible.

In one embodiment, the server 141 includes modules to monitor 142, analyze 143, and alert 146. The server 141 is coupled to a database 147 or other form of structured data store, within which patient data 148 is maintained. Other modules are possible.

The monitor module 142 regularly obtains physiometry 153 and parametric data 154 from patient CRM devices, which are saved as patient data 148 into a corresponding patient record in the database 147. The physiometry 153 and parametric data 154 can be requested, or "pulled," from each CRM device, or unilaterally sent, or "pushed." In addition, the physiometry 153 and parametric data 154 may be forwarded from an intermediary device, such as CRM device-originated physiometry, which has been locally interrogated by a repeater that is uploading the physiometry to the server 141. Other physiometry monitoring arrangements are possible.

The analysis module 143 can include an episode submodule 144 for evaluating AT episodes 149, as described above with reference to FIG. 5. The analysis module 143 can include a counter submodule 145 for evaluating total AT mode switch time (MST) 150, lifetime maximum AT duration counter 151, and reset maximum AT duration counter 152, as described above beginning with reference to FIG. 6. Other analysis functions are possible.

Finally, the alert module 146 generates alert messages 155 when atrial arrhythmia burden exceeding threshold values can be determined. In a further embodiment, the alert messages 155 reflect a user-configurable number of hours in a 24-hour or other period of atrial arrhythmia to trigger notification. For instance, where a twelve hour notification trigger (atrial arrhythmia burden threshold) is specified, an alert message 155 based on the AT episodes 149 could be created as:

Atrial Arrhythmia Burden of at least 12 hours in a 24 hour period on 29 Apr. 2007. Reference Arrhythmia Logbook within the Events tab for details.

Similarly, an alert message 155 based on the total AT mode switch time (MST) 150, lifetime maximum AT duration counter 151, and reset maximum AT duration counter 152 could be created as:

Atrial Arrhythmia Burden of at least 12 hours in a 24 hour period between 22 Apr. 2007 and 29 Apr. 2007.

Other alerts are possible.

Figure 11:
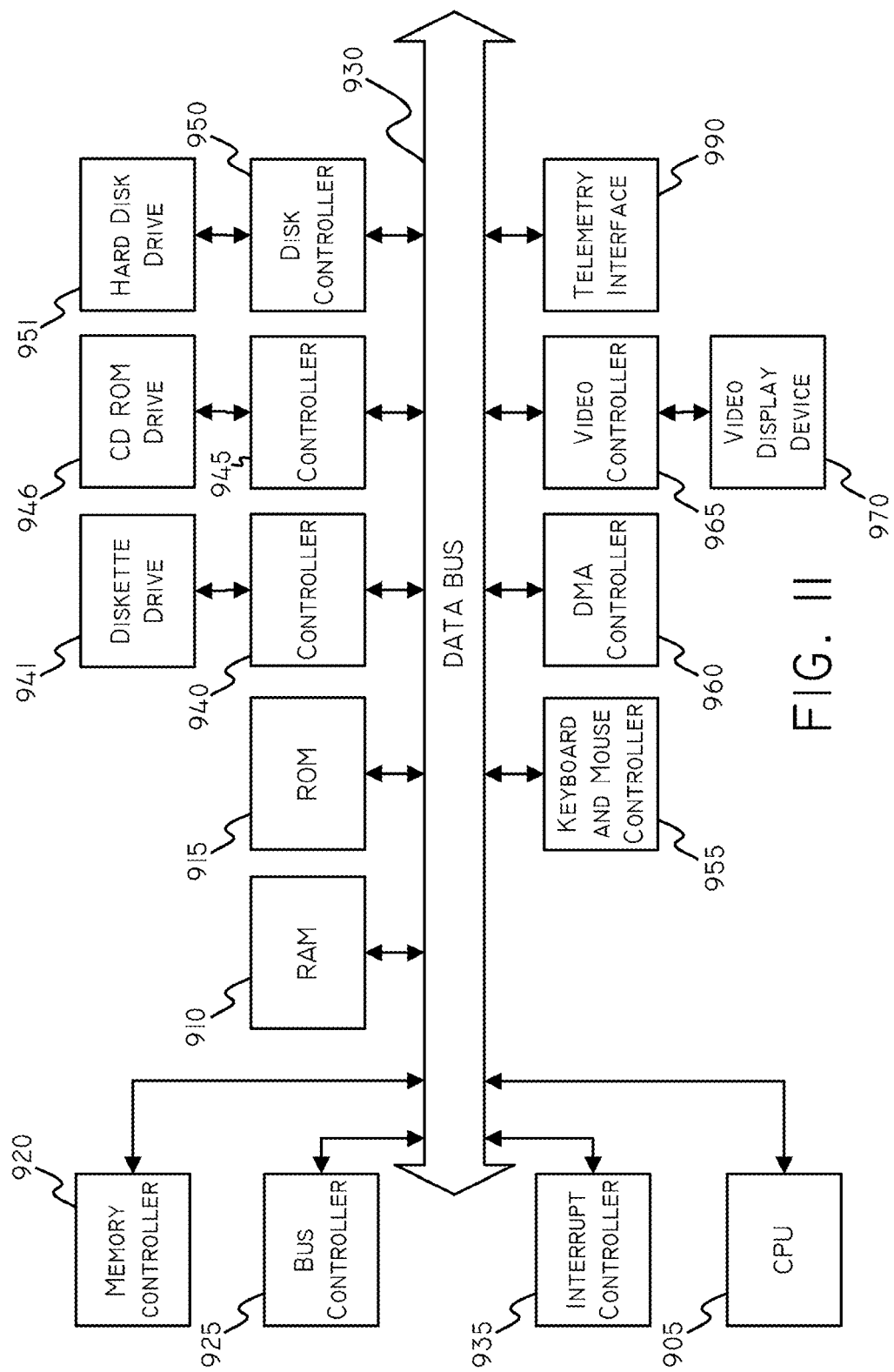
FIG. 11 is a block diagram of components that can be included with an external patient management system.

It will be appreciated that external patient management systems of various embodiments can include a variety of specific components in order to carry out specific functions, methods, and/or modules as described herein. Referring now to FIG. 11, a diagram of various components that can be included as part of an external patient management system is shown in accordance with at least some embodiments. The system can include a central processing unit (CPU) 905 or processor, which may include a conventional microprocessor, random access memory (RAM) 910 for temporary storage of information, and read only memory (ROM) 915 for permanent storage of information. A memory controller 920 can be provided for controlling system RAM 910. A bus controller 925 can be provided for controlling data bus 930, and an interrupt controller 935 can be provided for receiving and processing various interrupt signals from the other system components.

In some embodiments, mass storage can be provided by diskette drive 941, which is connected to bus 930 by controller 940, CD-ROM drive 946, which is connected to bus 930 by controller 945, and/or hard disk drive 951, which is connected to bus 930 by controller 950. In various embodiments the external patient management system can include data storage provided by a database, either integrated with or separated from, but in networked communication, other components of the external patient management system. Where applicable, user input to the system can be provided by a number of devices. For example, a keyboard and mouse can be connected to bus 930 by keyboard and mouse controller 955. DMA controller 960 can be provided for performing direct memory access to system RAM 910. A visual display can be generated by a video controller 965, which controls video display 970. In some embodiments, the system can also include a telemetry interface 990 or telemetry circuit which allows the system to interface and exchange data with an implantable medical device. In some embodiments, the system can include a networking interface which allows the system to be in networked communication with other components that may be part of the external patient management system or with devices and/or systems outside of the external patient management system. It will be appreciated that in various embodiments not all of the components depicted in FIG. 11 may be present. Further, in various embodiments, some of the components can be integrated together.

The methods illustrated in this disclosure are not intended to be exclusive of other methods within the scope of the present subject matter. Those of ordinary skill in the art will understand, upon reading and comprehending this disclosure, other methods within the scope of the present subject matter.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled. While the invention has been particularly shown and described as referenced to the embodiments thereof, those skilled in the art will understand that the foregoing and other changes in form and detail may be made therein without departing from the spirit and scope of the invention.

What is claimed is:

1. An external patient management system for determining atrial arrhythmia burden, comprising:
    an external database configured to centrally maintain sets of parametric data obtained from an implantable medical device through interrogation;
    the external patient management system configured to execute an analysis module to calculate an atrial arrhythmia burden, the analysis module comprising:
        an episode submodule configured to identify a cumulative atrial tachyarrhythmia duration for each atrial tachyarrhythmia episode recorded in the parametric data over a look back period, wherein the duration of the look back period is measured from the time of the end of each atrial tachyarrhythmia episode if the atrial tachyarrhythmia episode has concluded before interrogation of the implanted device or from the time of interrogation of the implanted device if the most recent atrial tachyarrhythmia episode is still in progress at the time of interrogation; and
        a counter submodule configured to evaluate therapy duration counter data obtained from the implantable medical device.

2. The system of claim 1, wherein the look back period comprises 12 hours.

3. The system of claim 1, wherein the look back period comprises 24 hours.

4. The system of claim 1, wherein the counter submodule only evaluates therapy duration counter data obtained from the implantable medical device if the analysis module fails to calculate an atrial arrhythmia burden exceeding a threshold value based on cumulative atrial tachyarrhythmia durations for each atrial tachyarrhythmia episode recorded in the parametric data over a look back period.

5. The system of claim 1, the therapy duration counter data comprising at least one selected from the group consisting of total atrial tachyarrhythmia mode switch time, lifetime maximum atrial tachyarrhythmia duration, and reset maximum atrial tachyarrhythmia duration.

6. The system of claim 5, wherein lifetime maximum atrial tachyarrhythmia duration is only evaluated if the analysis module fails to calculate an atrial arrhythmia burden exceeding a threshold value based on evaluation of total atrial tachyarrhythmia mode switch time.

7. The system of claim 6, wherein reset maximum atrial tachyarrhythmia duration is only evaluated if the analysis module fails to calculate an atrial arrhythmia burden exceeding a threshold value based on evaluation of lifetime maximum atrial tachyarrhythmia duration.

8. The system of claim 5, wherein a user-specifiable length of time must have elapsed between consecutive interrogations of the implantable medical device in order for the external patient management system to determine that an atrial arrhythmia burden threshold has been met.

9. The system of claim 5, further comprising:
    an evaluation submodule configured to select the lifetime maximum atrial tachyarrhythmia duration counter value comprised in the most recent parametric data set as an atrial tachyarrhythmia duration for calculation of atrial arrhythmia burden, if the value of the lifetime maximum atrial tachyarrhythmia duration counter is greater than a recorded lifetime maximum atrial tachyarrhythmia duration counter value from a previous implantable medical device interrogation.

10. The system of claim 5, further comprising:
    an evaluation submodule configured to select the reset maximum atrial tachyarrhythmia duration counter value comprised in the most recent parametric data set as an atrial tachyarrhythmia duration for calculation of atrial arrhythmia burden, if the value of the reset maximum atrial tachyarrhythmia duration counter is greater than a recorded reset maximum atrial tachyarrhythmia duration counter value from a previous implantable medical device interrogation.

11. The system of claim 1, the analysis module configured to generate an atrial arrhythmia burden alert if the atrial arrhythmia burden as calculated by the analysis module exceeds a threshold value.

* * * * *